United States Patent [19]

Peacock et al.

[11] 4,427,633

[45] Jan. 24, 1984

[54] GAS MIXING APPARATUS FOR METASTABLE TRANSFER EMISSION SPECTROSCOPY

[75] Inventors: Jon R. Peacock, Mission Viejo; Robert L. Schmidt, Placentia, both of Calif.

[73] Assignee: Beckman Instruments, Inc., Fullerton, Calif.

[21] Appl. No.: 165,529

[22] Filed: Jul. 3, 1980

[51] Int. Cl.³ ............................................. G01N 21/76
[52] U.S. Cl. .................................. 422/83; 250/361 C; 422/52; 422/86; 422/90; 436/35; 436/164
[58] Field of Search .................... 23/232 R, 232 E; 422/52, 83, 86; 250/361 R, 361 C; 73/421.5 R; 372/55, 58, 59, 70, 89, 90; 436/35, 164

[56] References Cited

U.S. PATENT DOCUMENTS

| | | | |
|---|---|---|---|
| 3,571,747 | 3/1971 | Bronfin et al. | 372/58 |
| 3,600,704 | 8/1971 | Banas | 372/58 |
| 3,646,475 | 2/1972 | Taylor | 372/58 |
| 3,734,761 | 5/1973 | Becker et al. | 422/158 |
| 3,735,000 | 5/1973 | Calcagno et al. | 422/158 |
| 3,832,650 | 8/1974 | Roberts | 372/89 |
| 4,013,415 | 3/1977 | Burov et al. | 422/186 |
| 4,049,383 | 9/1977 | Burton et al. | 23/232 E |
| 4,119,509 | 10/1978 | Szoke | 422/186 |
| 4,148,612 | 4/1979 | Taylor et al. | 23/232 R |
| 4,150,951 | 4/1979 | Capelle et al. | 23/232 E |
| 4,315,894 | 2/1982 | Austin | 422/158 |

OTHER PUBLICATIONS

Melzer et al., "Det. of Trace Amounts of Lead in Water by Metastable Transfer Emission Spec.", Anal. Chem., vol. 52, p. 348, (Feb. 1980).
Capelle et al., "Metastable Transfer Emission Spec: Method and Instrum. for Detect . . . in Gas Flows", Aerospace Rep. No. ATR-78 (8227)-1, Mar. 30, 1978.
Drithler et al., "Excitation of Group Ia and IIb Metal Atoms by a Lewis-Rayleigh Nitrogen Afterglow", J. of Chemical Physics, vol. 59, p. 167 (1973).

*Primary Examiner*—Michael S. Marcus
*Attorney, Agent, or Firm*—Robert J. Steinmeyer; Robert R. Meads; Steven R. Markl

[57] ABSTRACT

For use in a system for analyzing sample constituents by metastable transfer emission spectroscopy, an improved apparatus for mixing a sample gas with a metastable gas. The apparatus provides an unobstructed path for the flow of sample gas so as to minimize deposition of the sample on walls of the apparatus. The apparatus may comprise an annular manifold coaxially mounted around a conduit through which flows the sample, or it may comprise a collar detachably connected in line with such a conduit.

8 Claims, 5 Drawing Figures

GAS MIXING APPARATUS FOR METASTABLE TRANSFER EMISSION SPECTROSCOPY

BACKGROUND OF THE INVENTION

1. Field of the Invention

The present invention broadly relates to apparatus for exciting the atoms of a sample gas to higher atomic energy levels by transferring energy to the sample from a metastable gas. Such apparatus commonly is used for metastable transfer emission spectroscopy. More particularly, the present invention is directed to apparatus for mixing the sample gas with the metastable gas.

2. Description of the Prior Art

Metastable transfer emission spectroscopy (MTES) is a recently developed method of analyzing the elemental composition of a solid, liquid or gaseous sample. The method is described in U.S. Pat. No. 4,148,612 to Taylor et al.; U.S. Pat. No. 4,150,951 to Capelle et al.; and Aerospace Report No. ATR-78(8227)-1 by Capelle and Sutton entitled "Metastable Transfer Emission Spectroscopy: Method and Instrument for Detection and Measurement of Trace Material in Gas Flows," dated Mar. 30, 1978.

MTES involves the use of metastable gas, which may be defined as a gas having a substantial number of its atoms or molecules excited to atomic or molecular energy levels above the ground state, wherein the atoms or molecules remain in their excited states for a relatively long time, generally for a time ranging from a microsecond to a few seconds. Typically, the metastable gas is created by using a electromagnetic field to directly or indirectly excite a stable gas such as nitrogen or one of the noble gases.

In MTES, if the sample to be analyzed is not in gaseous form, it must be vaporized by some means. Various sample vaporization means are known in the art. In some cases the sample gas is entrained in an inert carrier gas, but such a combination will simply be referred to herein as the sample gas.

The sample gas and the metastable gas are directed to flow into a common mixing region. Upon mixture with the metastable gas, the atoms or molecules of the sample gas become excited to energy levels above the ground state via energy transfer from molecular collisions with excited metastable gas molecules. After being excited, the sample atoms or molecules almost immediately give up their excess atomic energy by emitting a photon of light and returning to the unexcited ground state. A spectrometer placed outside a transparent window near the mixing region analyzes the light emitted by the excited sample atoms. The wavelength and intensity of the emitted light respectively identify and quantify the constituents of the sample.

A critical component of any MTES system is the mixing means comprising the mixing region and the associated apparatus for mixing the sample gas with the metastable gas. One important requirement of the mixing means is that it must mix the two materials thoroughly enough so that the sample gas is exposed to and excited by the metastable gas with consistent efficiency. The Capelle patent discloses that this is so critical that the prior investigators' failure to develop the MTES technique may have been due to their ineffective means for dispensing the sample into the metastable gas flow.

Another important requirement of the mixing means is that it must minimize the amount of sample that is deposited on the walls of the apparatus instead of being mixed with the metastable gas. To the extent such deposition occurs, the number of excited sample atoms or molecules will be reduced, and hence the accuracy and sensitivity (i.e., the minimum detectable sample quantity) will be degraded. This requirement is difficult to satisfy because the sample atoms or molecules tend to adhere to any surfaces they contact.

The Capelle patent and the Capelle and Sutton report both disclose a mixing means which may be described as follows. The sample is vaporized in a furnace and swept up a vertical quartz glass tube by a carrier gas. A donut-shaped hollow ring, also made of quartz glass, is coaxially mounted within the tube above the furnace. The metastable gas is pumped through a length of ducting into the donut-shaped interior of the ring. From there, the metastable gas is injected into the tube through eight holes circumferentially spaced along the upward (i.e., downstream) surface of the donut and pointing slightly inward.

The Capelle mixing means has at least two disadvantages arising from the placement of the donut-shaped ring within the interior of the quartz tube. One disadvantage is that the ring partially obstructs the flow of sample gas through the quartz tube so that some of the sample may be deposited on the surface of the ring instead of mixing with the metastable gas. As discussed earlier, this would reduce the sensitivity of the instrument to small sample quantities. Another disadvantage is the impracticality of constructing a hollow ring within a quartz tube much smaller than the nine centimeter diameter tube described by Capelle. It is generally desirable to use smaller tubes to minimize the bulk of the apparatus.

Another disadvantage of the Capelle mixing means is that constructing the ring and mounting it within the tube are intricate, time-consuming, and expensive. Furthermore, the finished apparatus is very delicate and easily damaged.

A substantially different mixing means is disclosed in Duthler and Broida, "Excitation of Group Ia and IIb metal atoms by a Lewis Rayleigh nitrogen afterglow," *Journal of Chemical Physics,* Vol. 59, No. 1, pp. 167–174 (1973). The sample is vaporized in a furnace and swept upwards through the bottom of a stainless steel mixing chamber by a carrier gas. A Pyrex glass tube oriented perpendicular to the direction of sample gas flow extends from a point near the center of the mixing chamber to a source of metastable gas outside the chamber. The metastable gas is pumped through the Pyrex tube and enters the mixing chamber through a small orifice in the tube.

Duthler and Broida did not describe their apparaus a being useful for quantitative analysis of a sample. Instead, they disclosed using the apparatus to investigate the physics underlying the excitation of metal atoms by observing the relative intensities and pressure dependence of spectral lines. Since they were concerned only with measuring relative intensities instead of absolute intensities, their apparatus includes features that make it unsuitable for quantitative analysis by MTES. For example, the Pyrex tube through which the metastable gas is injected into the sample gas obstructs the sample flow so that a substantial fraction of the sample will be deposited thereon. In addition, their mixing chamber is composed of stainless steel, which will deactivate much of the metastable gas.

The Taylor patent does not describe any particular structure for the mixing means. It is depicted in the drawings only in generalized schematic form.

SUMMARY OF THE INVENTION

The present invention is an apparatus for exciting the atoms of a sample gas to atomic energy levels above the ground state by transferring energy to the sample from a metastable gas. The apparatus according to the present invention includes an improved means for mixing the sample gas with the metastable gas comprising one or more of the following features.

The features are defined in terms of a first gas and a second gas, one of the two gases being the sample gas, and the other being the metastable gas.

One feature is that the first gas flows through a conduit into which the second gas is injected by means which does not protrude into the interior of the conduit. An advantage of this feature is that it prevents the sample vapor from being deposited on the injection means. As explained earlier, such depositions would reduce the sensitivity of the instrument.

Another feature is that the first gas is conveyed through a conduit having two sections detachably connected together through a coupler. The second gas is conveyed into the coupler whereupon it mixes with the first gas. Advantages of this detachable arrangement include the ease of substituting different couplers employing different mixing configurations and the ease of replacing dirty or damaged conduit sections or mixing apparatus. Such substitutions and replacements are very cumbersome and time-consuming in prior art designs.

A further feature is that the first gas flows through a flow tube around which is coaxially positioned an exterior manifold. The second gas flows through the manifold, and then enters the flow tube through a plurality of openings from the manifold. Unlike prior art annular manifolds, such a manifold does not occupy space within the flow tube. One resulting advantage is that the sample vapor will not be deposited on the manifold surface, thereby increasing the sensitivity of the instrument for the reasons explained earlier. Another resulting advantage is that the manifold according to the present invention may readily be constructed to fit less cumbersome small diameter flow tubes.

DESCRIPTION OF THE PREFERRED EMBODIMENTS

Figure 1:
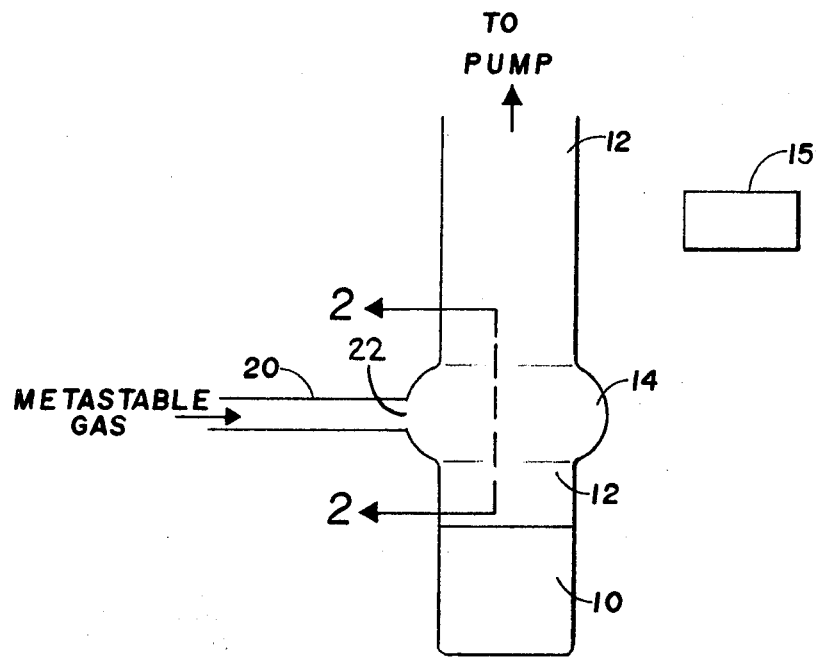
FIG. 1 is a side view of an embodiment of the invention having an annular manifold surrounding a flow tube.

FIG. 1 shows one embodiment of an instrument according to the present invention for quantitative and qualitative analysis of a sample by metastable transfer emission spectroscopy (MTES). Generally, the instrument comprises sample source 10, flow tube 12, annular manifold 14, and spectrometer 15.

Sample source 10 for supplying the sample gas may be any of the conventional sources described in the references cited in the Background of the Invention. If the sample is not originally in gaseous form, the sample source vaporizes it. A vacuum pump, not shown, connected to the upper end of quartz flow tube or conduit 12, draws the sample gas up through flow tube 12.

As the sample vapor travels up flow tube 12, it passes annular manifold 14. Metastable gas, supplied by a source not shown, is injected from manifold 14 through openings 18 (see FIG. 2) into the interior of flow tube 12 so as to mix with the sample gas. The metastable gas transfers energy to the sample gas so as to excite the sample atoms or molecules to higher energy levels. The excited sample atoms or molecules return to the ground state by emitting light whose wavelengths and intensity are measured by spectrometer 15 placed adjacent to flow tube 12 just above (i.e., just downstream from) manifold 14. After flowing past the spectrometer, the gases are exhausted out the top of flow tube 12 by the vacuum pump, not shown.

Manifold 14 comprises a hollow torus or annulus positioned coaxially around quartz flow tube or conduit 12. Manifold 14 preferably is fabricated by glass blowing so as to be an integral part of flow tube 12. Although a slight inward curvature of the manifold's inner wall 16 is difficult to avoid in the glass blowing process, it can be minimized so that inner wall 16 has substantially the same diameter as flow tube 12, and hence does not protrude substantially into the interior of the flow tube. Eight circumferentially spaced ports or openings 18 penetrate inner wall 16 of manifold 14 to permit fluid communication between the interior 17 of manifold 14 and the interior of flow tube 12.

Metastable gas is supplied to manifold 14 from a conventional source such as those described in the cited references. For example, metastable gas may be created by passing nitrogen gas through a microwave cavity. The metastable gas flows through duct 20 and enters the hollow interior 17 of manifold 14 through opening 22. From the interior of manifold 14, the metastable gas enters the interior of flow tube 12 through ports or openings 18.

One feature distinguishing manifold 14 from prior art annular manifolds such as the ring injector disclosed in the cited references by Capelle is that manifold 14 is positioned outside of flow tube 12. One advantage of this feature is that the sample gas flowing through tube 12 is not obstructed by manifold 14, and hence none of the sample is deposited on the manifold. As discussed in the Background of the Invention, it is advantageous to prevent any amount of sample from being deposited on the walls of the apparatus because such deposition reduces the number of sample atoms or molecules available for excitation by the metastable gas, and hence reduces the sensitivity of the instrument.

Another advantage of this feature is that it facilitates the use of flow tubes 12 having diameters much smaller than the nine centimeter diameter tube described by Capelle because it is much easier to construct an annular manifold around the outside of a small flow tube than inside the tube. It generally is desirable to use smaller flow tubes to reduce the bulk of the apparatus.

The just described embodiment of the invention has been shown to have various advantages over prior art annular manifolds. Nevertheless, it retains some of the shortcomings of the prior art manifolds. One such shortcoming is the difficulty of repairing it when parts thereof became dirty or damaged. For example, the flow tube requires replacement from time to time because sample deposits slowly accumulate on its inner walls. In addition, the glass flow tube and the delicate blown glass manifold are susceptible to accidental breakage.

Figure 3:
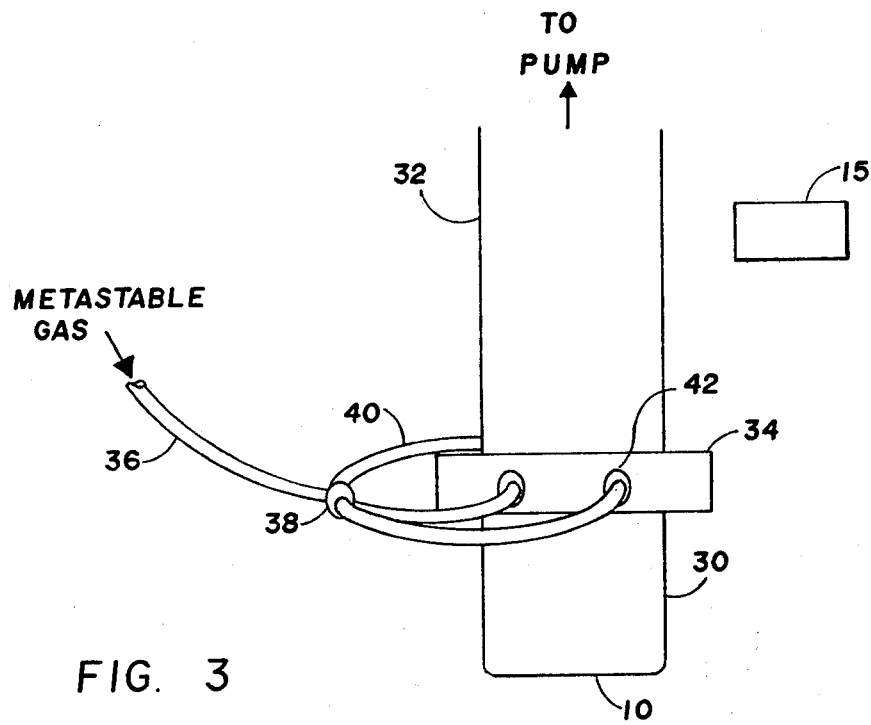
FIG. 3 is a side view of the preferred embodiment of the invention comprising a detachable collar.

The preferred embodiment of the present invention, shown in FIG. 3, has several features which overcome the shortcomings of the embodiment just described.

The preferred embodiment shown in FIG. 3 comprises a sample source 10 which may be any of the conventional means for supplying sample gas, as discussed earlier. The upper end of sample source 10 comprises a short conduit section 30 out of which flows the sample gas.

Conduit section 30 of sample source 10 connects to a conduit comprising an injection collar 34 and an upper conduit section 32. The inner wall of injection collar 34 is contiguous and in a straight line with the inner walls of conduit section 32 so that the two components in combination constitute a single conduit having no internal protrusions to interfere with the flow of sample gas therethrough.

In operation, a vacuum pump, not shown, connects to the upper end of upper conduit section 32 and causes the sample gas to flow out of sample source 10, through the interior 44 of injection collar 34, and through upper conduit section 32.

Simultaneously, a source of metastable gas, not shown, supplies metastable gas through duct 36, fitting 38, and three ducts 40 to three ports or openings 42 spaced circumferentially around injection collar 34. The metastable gas enters the interior 44 of injection collar 34 through the three ports 42, whereupon it mixes with the sample gas flowing upwardly through interior 44. As described earlier, the sample atoms or molecules become excited and emit light upon contact with the metastable gas. The light emission is analyzed by spectrometer 15 placed adjacent to upper conduit section 32 just above injection collar 34.

Figure 2:
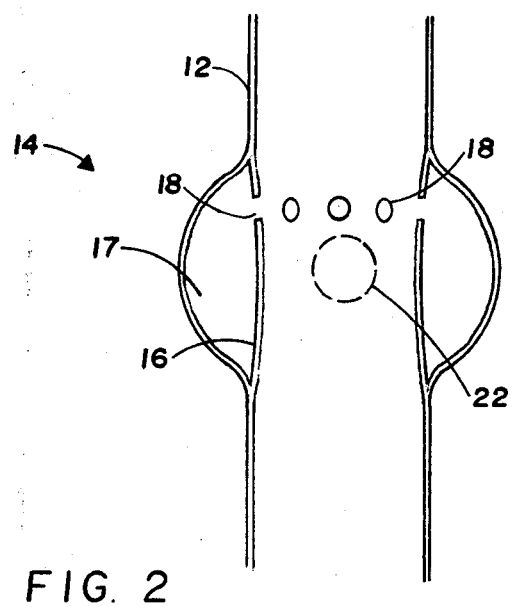
FIG. 2 is a sectional view along the line 2—2 in FIG. 1.
Figure 4:
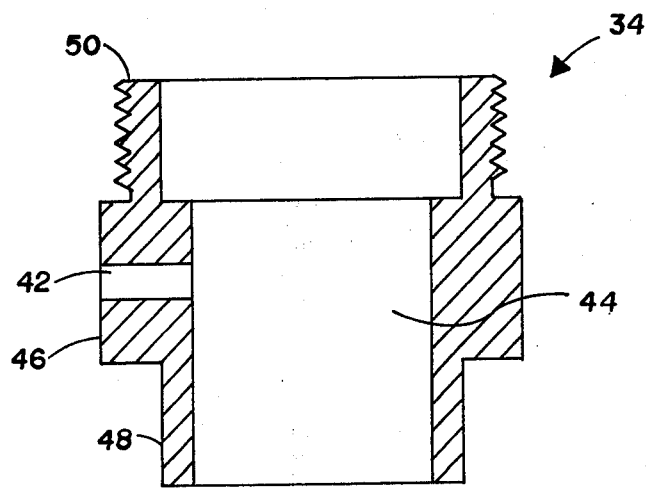
FIG. 4 is a sectional view of the detachable collar alone.

Unlike annular manifold 14 shown in FIGS. 1 and 2, injection collar 34 shown in FIG. 3 has no hollow torus which metastable gas must enter before being injected into the conduit or flow tube. As shown more clearly in FIGS. 4 and 5, injection collar 34 comprises a solid annular body 46 having annular flanges 48 and 50 extending axially from opposite sides thereof. The three circumferentially spaced ports or openings 42 are simply three holes extending radially through body 46.

Injection collar 34 may be fabricated inexpensively by machining a single piece of solid plastic. In contrast, the only feasible method of fabricating the hollow torus of manifold 14 is by the more expensive process of glass blowing. Furthermore, injection collar 34 is practically unbreakable because of its plastic composition, whereas blown glass manifold 14 is highly fragile.

Applicants' tests indicate that simply injecting metastable gas through the three ports 42 of injection collar 34 excites the sample atoms just as effectively as using the more elaborate annular manifold or injection ring. In fact, applicants have successfully used the apparatus shown in FIG. 3 with a plug inserted in two of the three ports 42 so that metastable gas was injected through only a single port.

Another advantageous feature of injection collar 34 is that it may be quickly and easily connected or disconnected to conduit sections 30 and 32 and metastable gas ducts 40.

Figure 5:
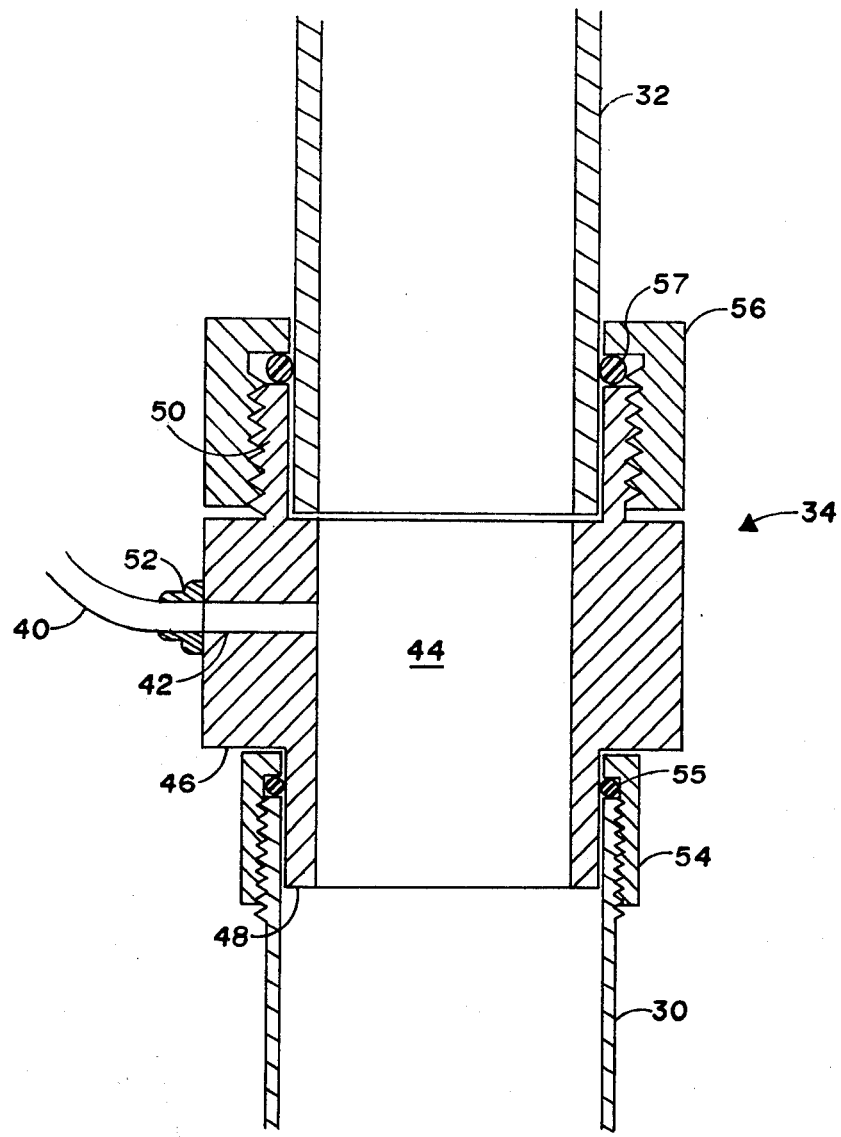
FIG. 5 is a sectional view of the collar, the conduits, and the connecting hardware.

As shown in FIG. 5, each duct 40 preferably consists of a length of flexible tubing terminated by a threaded fitting 52. Each port 42 of injection collar 34 preferably is threaded so that a duct 40 may be connected or disconnected to a port 42 by simply screwing fitting 52 into or out of the port.

FIG. 5 also shows the preferred means for detachably connecting injection collar 34 to conduit sections 30 and 32. To connect injection collar 34 to conduit section 30 of sample source 10, nut 54 and O-ring 55 are slipped over lower flange 48 until they abut body 46. There is sufficient friction between O-ring 55 and lower flange 48 to hold nut 54 against body 46. Injection collar 34 is then placed over the threaded top of conduit section 30 so that the threaded portion fits between lower flange 48 and nut 54 of the injection ring. Finally, nut 54 is tightened down on the threads of conduit section 30 until O-ring 55 is compressed sufficiently to create a seal among lower flange 48, nut 54, and conduit section 30. Injection collar 34 may be disconnected from sample source 10 at any time by simply loosening nut 54 to relax O-ring 55.

Upper conduit section 32 connects to injection collar 34 in a similar manner. First, nut 56 and O-ring 57 are slipped over the lower end of upper conduit section 32. The lower end of conduit section 32 is then concentrically placed within threaded upper flange 50 so that it rests on body 46 of injection collar 34. The final step is to tighten down nut 56 over the threaded upper flange 50 to sealingly compress O-ring 57 against upper conduit section 32, nut 56, and upper flange 50. Upper conduit section 32 may be disconnected from injection collar 34 at any time by simply loosening nut 56 to relax O-ring 57.

Because conduit sections 30 and 32 and injection collar 34 are so readily connected and disconnected, it is easy to replace any component that may become dirty or broken. This arrangement also facilitates component substitutions for experimental purposes or to perform different types of analyses.

In summary, the preferred embodiment shown in FIG. 3 has many advantageous features. Its means for injecting metastable gas into the sample vapor comprises an injection collar whose walls are contiguous with those of the conduit or flow tube to prevent undesirable sample deposition and minimize turbulence. The injection collar is readily detachable from all tubes and ducts to which it connects, facilitating component replacement. The injection collar may be inexpensively machined from plastic and is practically unbreakable.

We claim:

1. In combination with an analyzing means for analyzing a sample material constituent in a first gas, means defining a supply of said first gas, generating means for exciting a gas to a metastable state, means defining a supply of a second gas, and means for supplying said second gas to said generating means;

means for mixing an excited metastable second gas in said first gas to transfer energy from said metastable gas to molecules of a sample material carried in said first gas causing characteristic spectral emission, said mixing means comprising:

conduit means connected to and in fluid communication with said analyzing means, having a wall defining a primary channel of uniform cross section through which one of said first or second gases is conveyed from means supplying said gas;

a manifold means exterior to said conduit means defining a secondary channel for conveying the other of said first or second gases, from said means supplying said gas into said primary channel of said conduit means, to mix said gases, said secondary channel having an exit portion communicating with said primary channel through a plurality of openings in said wall of said conduit means, said exit portion opening through said conduit wall in a manner to provide an unobstructed primary channel of uniform cross section, and to direct said gas conveyed by said manifold means into the unobstructed flow of the other of said gases conveyed by said conduit means to mix said gases together for reaction and analysis.

2. The mixing means according to claim 1, wherein said conduit means comprises:
a first conduit portion;
a second conduit portion; and
a hollow coupler detachably connected said first and second conduit portions, said coupler having an interior surface combining with the interior surface of one of the other of said first and second conduit portions to provide a smooth interior wall defining a uniform cross sectional areas for gas flow through said coupler and said conduit portion without obstruction, and said coupler having a plurality of spaced openings through which said exit portions of said secondary channels communicate to convey one of said first or second gases into the other of said gases for mixing.

3. In combination with an analyzing means for analyzing a sample material constituent in a first gas, means defining a supply of said first gas, generating means for exciting a gas to a metastable state, means defining a supply of a second gas, and means for supplying said second gas to said generating means;
means for mixing an excited metastable second gas to said first gas to transfer energy from said metastable gas to molecules of a sample material carried in said first gas causing characteristic spectral emission, said mixing means comprising:
first and second conduit sections;
a detachable coupler, centrally positioned and connecting said two conduit sections to permit fluid communication between said conduit sections and through said coupler without obstruction, said coupler including a plurality of peripherally spaced openings for conveying a gas from outside said coupler to the interior of said coupler;
means connected to one of said generating means or said first gas supply means for conveying one of said first or second gases through said first conduit section, through the coupler, and then through said second conduit section to said analyzing means; and
means connected to the other of said generating means or said first gas supply means for conveying the other of said first or second gases into the interior of the coupler through said openings so as to mix said gases.

4. In combination with an analyzing means for analyzing a sample material constituent in a first gas, means defining a supply of said first gas, generating means for exciting a gas to a metastable state, means defining a supply of a second gas, and means for supplying a second gas to said generating means;
means for mixing an excited metastable second gas in said first gas to transfer energy from said metastable gas to molecules of a sample material carried in said first gas causing characteristic spectral emission, said mixing means comprising:
a flow tube having a substantially uniform cross sectional area through which flows one of said first or second gases;
an annular manifold positioned coaxially around the exterior of said flow tube, having an inner diameter formed by said flow tube, and having a hollow interior space in fluid communication through a plurality of openings with the interior of said flow tube, and having an additional opening in fluid communication with a means for supplying the other of said first or second gases, including means for conveying said gas from its supply means through the additional opening, into the hollow interior of the manifold, through the plurality of openings, and into the interior of the flow tube, whereby the second gas mixes with the first gas and obtains spectral reaction.

5. In combination with an analyzing means for analyzing a sample material constituent in a first gas, means defining a supply of said first gas, generating means for exciting a gas to a metastable state, means defining a supply of a second gas, and means for supplying said second gas to said generating means;
means for mixing an excited metastable second gas with a first gas to transfer energy from said metastable gas to molecules of a sample material carried in said first gas causing characteristic spectral emission, said mixing means comprising:
an annular wall defining an interior volumetric space, said annular wall having a substantially cylindrical interior portion, a plurality of openings formed through said cylindrical interior portion of said annular wall to provide fluid communication between said volumetric space within said annular wall and a space central to said annular wall, an opening formed through an outer portion of said annular wall to provide fluid communication with said volumetric space within said annular wall, a first flow tube connected to said annular wall having an interior surface combining with said cylindrical interior portion of said annular wall to form an unobstructed conduit for a gas, a second flow tube connected to the opposing side of said annular wall, having an interior surface combining with said cylindrical interior portion of said annular wall to form an unobstructed conduit for a gas, whereby one of said first or second gases is flowed through said flow conduit and the other of said gases is flowed through said outer opening of said annular wall and through said plurality of openings formed through said interior portion of said annular wall to mix said gases without obstruction of flow within said flow conduit.

6. The mixing apparatus of claim 5, wherein said first flow tube and second flow tube are detachably and sealingly connected to said annular wall.

7. In combination with an analyzing means for analyzing a sample material constituent in a first gas, means defining a supply of said first gas, generating means for exciting a gas to a metastable state, means defining a supply of a second gas, and means for supplying said second gas to said generating means;

means for mixing an excited metastable second gas in said first gas to transfer energy from said metastable gas to molecules of a sample material carried in said first gas causing characteristic spectral emission, said mixing means comprising:

a circular collar having a cylindrical interior wall, said collar having detachable sealing connectors on each end for detachably connecting tubular members to define an interior space for flowing one of said first or second gases, and said collar having a plurality of spaced ports formed laterally therethrough providing openings for flowing the other of said gases into the interior of said collar and said tubular members in assembly, said interior wall of said collar sized in diameter to match the interior diameter of at least one of said tubular members to provide a smooth flow path and uniform cross sectional area, and having an interior wall surface for an unobstructed flow path and uniform cross sectional area surrounding said port openings.

8. The apparatus of claim 7 additionally comprising at least one secondary manifold tube detachably and sealingly connected at one end to an outward end of said port in said collar, and having an opposing end connected for fluid communication with said source means of said first or second gases.

* * * * *